US012661171B2

(12) United States Patent
Jacob et al.

(10) Patent No.: US 12,661,171 B2
(45) Date of Patent: Jun. 23, 2026

(54) 'ELECTRICAL LEAK DETECTION SYSTEM' TO DETECT ABNORMAL CONDUCTION WITHIN A CATHETER IN THE PRESENCE OF ELECTRICAL INTERFERERS

(71) Applicant: Medtronic CryoCath LP, Toronto (CA)

(72) Inventors: Louis Jacob, Laval (CA); Timothy A. Ebeling, Circle Pines, MN (US); Harold M. Dyalsingh, Brooklyn Park, MN (US); Trenton J. Rehberger, Minneapolis, MN (US); Craig W. Dorma, Albertville, MN (US)

(73) Assignee: Medtronic CryoCath LP, Toronto (CA)

( * ) Notice: Subject to any disclaimer, the term of this patent is extended or adjusted under 35 U.S.C. 154(b) by 235 days.

(21) Appl. No.: 18/663,505

(22) Filed: May 14, 2024

(65) Prior Publication Data

US 2024/0299074 A1     Sep. 12, 2024

Related U.S. Application Data

(63) Continuation of application No. 17/315,592, filed on May 10, 2021, now Pat. No. 12,004,795.

(51) Int. Cl.
A61B 18/02 (2006.01)
A61B 18/00 (2006.01)
(52) U.S. Cl.
CPC .... A61B 18/02 (2013.01); A61B 2018/00351 (2013.01); A61B 2018/00708 (2013.01);
(Continued)

(58) Field of Classification Search
CPC ............ A61B 18/02; A61B 2018/0212; A61B 2018/00666; A61B 2018/00708; A61B 2018/00732; A61B 2018/00779
See application file for complete search history.

(56) References Cited

U.S. PATENT DOCUMENTS 9,539,046 B2    1/2017  Wittenberger
10,660,689 B2   5/2020  Fischer et al.
(Continued)

OTHER PUBLICATIONS

European Patent Office Extended Search Report for Application No. 22806147.9 dated Feb. 7, 2025 (7 pages).
(Continued)

*Primary Examiner* — Daniel W Fowler
(74) *Attorney, Agent, or Firm* — Michael Best & Friedrich LLP

(57)          ABSTRACT

A system, method and leak signal discriminator for detection of a leak or mechanical breach in a catheter shaft in the presence of an electrical interferer are disclosed. According to one aspect, a leak signal discriminator having a leak detection circuit is configured to distinguish between a leak signal arising from a leak in a catheter and an interfering signal arising from an electrical interferer. The leak signal discriminator includes circuitry configured to receive from the leak detection circuit a response signal responsive to a test signal the test signal having component signals, each component signal being at a different frequency, and distinguish between a leak and an electrical interferer based at least in part on an evaluation of the response signal.

16 Claims, 9 Drawing Sheets

(52) U.S. Cl.
    CPC ............... *A61B 2018/00898* (2013.01); *A61B*
                *2018/00922* (2013.01); *A61B 2018/0212*
                                        (2013.01)

(56)                    References Cited

U.S. PATENT DOCUMENTS

| 2015/0141978 | A1 | 5/2015 | Subramaniam et al. |
| 2015/0359558 | A1 | 12/2015 | Kardosh et al. |
| 2016/0367305 | A1 | 12/2016 | Hareland et al. |
| 2018/0153437 | A1 | 6/2018 | Schwartz et al. |

OTHER PUBLICATIONS

International Search Report and Written Opinion for Application
No. PCT/CA2022/050695 dated Aug. 8, 2022 (8 pages).

Processing Circuitry 44

Frequency Control 72

Gain Control 74

BPF Control 76

Leak Detection Threshold 78

Leak Alarm Receiver 80

ADCs 82

Leak Detection Algorithms 84

User Interface 45

Video Display 86

Leak Indication 92

Vosc 94

Vin 96

Keyboard 88

Mouse 90

'ELECTRICAL LEAK DETECTION SYSTEM' TO DETECT ABNORMAL CONDUCTION WITHIN A CATHETER IN THE PRESENCE OF ELECTRICAL INTERFERERS

CROSS-REFERENCE TO RELATED APPLICATION

This application is a continuation of and claims the benefit of U.S. patent application Ser. No. 17/315,592, filed May 10, 2021, the entire content of which is hereby incorporated in its entirety.

FIELD

The present technology is generally related to detection of leak or mechanical breach in a catheter shaft in the presence of an electrical interferer.

BACKGROUND

Catheters inserted and navigated through blood vessels are used to probe and treat a variety of medical conditions. For example, cardiac arrythmias may be treated by inserting a catheter into a blood vessel and guiding it to the heart. At the end of the catheter are electrodes for applying electrical energy and/or a solid metal tip or an inflatable balloon for applying cold fluid. The electrodes may detect electrical activity in tissue they contact and/or may deliver a pulsed electric field (PEF) to the tissue to disrupt electrical pathways in the tissue to treat the arrythmia. In a cryoablation catheter, the cardiac tissue is ablated using cryogenic fluid applied within a balloon near a distal end of the catheter. When both the balloon and the electrodes are present, the electrodes may be used to detect and map electrical activity in the tissue and then, when a target region of tissue is identified, the balloon of the cryoablation is inflated with cold fluid, causing contact between the balloon wall and the tissue, so that heat is drawn from the tissue, thereby disrupting electrical activity in the target tissue.

In a cryoablation catheter, fluid may unexpectedly leak into the catheter. Presence of fluid in the catheter may be detected by a leak detection circuit, which may include wires within the catheter which communicate a supervisory signal to electrodes located in the catheter-. If fluid enters the catheter and crosses conductive spots distributed along the electrodes, the current amplitude of the supervisory signal should increase. Circuitry is provided to monitor this supervisory current in the wires to detect the presence of amplitude modulation, and upon such detection, to indicate a leak. FIG. 1 shows a block diagram of conventional leak detection circuitry 10. A test signal generator 12 generates a sine wave at a frequency. This sine wave is carried on the aforementioned wires in the catheter which may be represented by a catheter equivalent circuit 14. The catheter equivalent circuit 14 may be modeled as a series RC circuit, where the resistance R is about 500 ohms and the capacitance C is about 200 pico-Farads (pF) when fluid is not present and greater than 500 pF when fluid is present. The catheter equivalent circuit 14 produces a response signal that is amplified by an amplifier 16. A peak in the amplified response signal is detected by a peak detector 18. The peak detector 18 may output a peak voltage that is compared to a threshold by a comparator 20. If the peak voltage exceeds the threshold, then the comparator output indicates a leak.

However, electrical interference signals may be present in the environment of the patient, as is usually the case in an operating room, for example. An electrical interference signal may couple to the wires in the catheter equivalent circuit 14 and interact with the response signal and be misinterpreted by the leak detection circuitry 10 as a fluid leak.

SUMMARY

The techniques of this disclosure generally relate to detection of a leak or mechanical breach in a catheter shaft in the presence of an electrical interferer.

In one aspect, the present disclosure provides a method of distinguishing between a leak signal arising from a leak in a catheter and an interfering signal arising from an electrical interferer. The method includes transmitting a test signal to a leak detection circuit of the catheter via wires within the catheter, the test signal having multiple component signals injected simultaneously, each component signal being at a different frequency with a known amplitude. The method also includes receiving from the leak detection circuit a response signal arising from modulation of the test signal by an environment within the catheter. The method further includes distinguishing between a leak and an electrical interferer based at least in part on an evaluation of the response signal.

According to this aspect, in some embodiments, distinguishing between a leak and an electrical interferer includes filtering the response signal at a first frequency of the different frequencies to produce a first filtered response signal. In some embodiments, distinguishing between a leak and an electrical interferer further includes: comparing the first filtered response signal to a first threshold. When the filtered response signal exceeds the first threshold, then the method includes filtering the response signal at a second frequency of the different frequencies to produce a second filtered response signal; comparing the second filtered response signal to a second threshold; and when the second filtered response signal exceeds the second threshold, then indicating a leak. In some embodiments, at least one of the first threshold and the second threshold is set according to a measure of noise power in the response signal. In some embodiments, the measured noise power for setting the first threshold is measured at a frequency that is different than the first frequency. In some embodiments, distinguishing between a leak and an electrical interferer includes passing the response signal through a filter configured to pass the response signal at one of the different frequencies and filter out the other frequencies of the different frequencies. In some embodiments, the filter is programmable to select a center frequency of the filter. In some embodiments, the filter is programmable to select an order of the filter. In some embodiments, distinguishing between a leak and an electrical interferer further includes turning off the test signal to determine whether the evaluation of the response signal indicates a presence of an electrical interferer when the test signal is turned off. In some embodiments, no component signal frequency is an integer multiple of any other of the component signal frequencies.

According to another aspect, a leak signal discriminator having a leak detection circuit configured to distinguish between a leak signal arising from a leak in a catheter and an interfering signal arising from an electrical interferer. The leak signal discriminator includes circuitry configured to receive from the leak detection circuit a response signal responsive to a test signal the test signal having component signals, each component signal being at a different frequency; and distinguish between a leak and an electrical interferer based at least in part on an evaluation of the response signal.

According to this aspect, in some embodiments, distinguishing between a leak and an electrical interferer includes filtering the response signal at a first frequency of the different frequencies to produce a first filtered response signal. In some embodiments, distinguishing between a leak and an electrical interferer further includes: comparing the first filtered response signal to a first threshold. When the first filtered response signal exceeds the first threshold, then, the response signal is filtered at a second frequency of the different frequencies to produce a second filtered response signal. The leak signal discriminator is configured to comparing the second filtered response signal to a second threshold, and when the second filtered response signal exceeds the second threshold, then indicating a leak. In some embodiments, at least one of the first threshold and the second threshold is set according to a measure of noise power in the response signal. In some embodiments, the measured noise power for setting the first threshold is measured at a frequency that is different than the first frequency. In some embodiments, the circuitry further includes a filter configured to pass the response signal at one of the different frequencies and filter out the signals at the other frequencies of the different frequencies. In some embodiments, the filter is programmable to select a center frequency of the filter. In some embodiments, the filter is programmable to select an order of the filter. In some embodiments, the circuitry further includes a peak detector configured to measure an amplitude peak of the response signal. In some embodiments, distinguishing between a leak and an electrical interferer further includes turning off the test signal to determine whether the evaluation of the response signal indicates a presence of an electrical interferer when the test signal is turned off.

According to yet another aspect, a cryoablation system is configured to distinguish between a leak signal arising from a leak in a catheter of the cryoablation system and an interference signal arising from an electrical interferer. The system includes a test signal generation circuit having a plurality of oscillators, each oscillator being configured to oscillate at a different frequency, no one of the different frequencies being an integer multiple of any other of the different frequencies. The system also includes a leak detection circuit located within the catheter and configured to: receive the test signal and, responsive to the test signal, and send a response signal to a leak signal discriminator circuit. The system also includes a leak signal discriminator circuit, the leak discriminator circuit configured to distinguish between a leak and an electrical interferer based at least in part on an evaluation of the response signal sent from the leak detection circuit, the evaluating being performed at each of multiple ones of the different frequencies.

According to this aspect, in some embodiments, the cryoablation system further includes a sampling circuit configured to simultaneously sample the test signal and the response signal and compare the sampled test signal to the sampled response signal. In some embodiments, the response signal is sampled at a rate that is an integer multiple of one of the different frequencies. In some embodiments, the response signal is sampled at a rate that is an integer multiple of one of the different frequencies but not an integer multiple of the other frequencies of the different frequencies.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
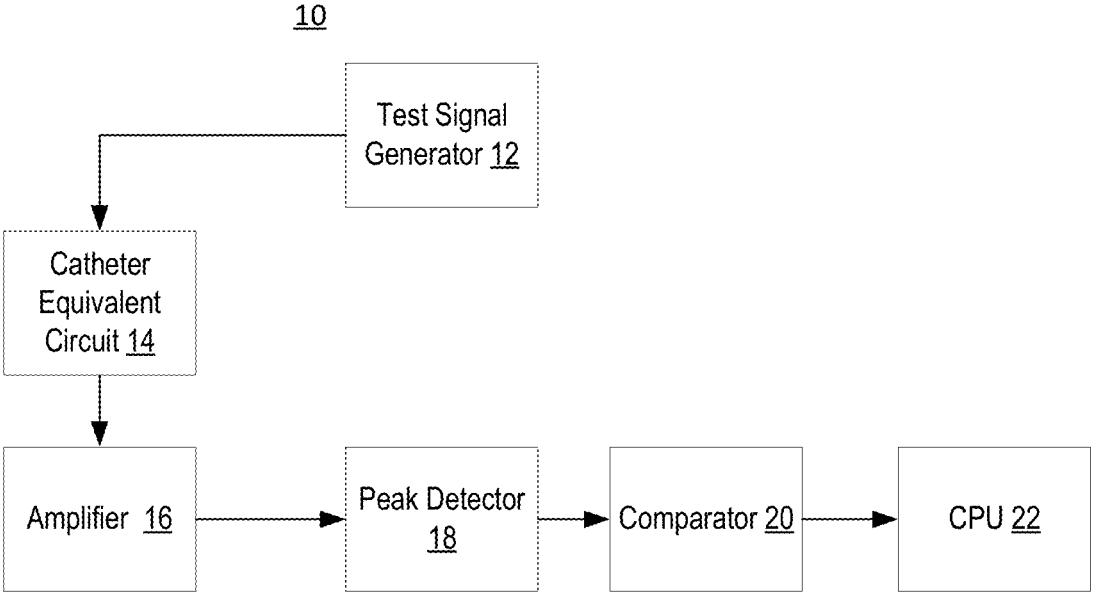
FIG. 1 is a block diagram of a known catheter leak detection system.

Before describing in detail exemplary embodiments, it is noted that the embodiments reside primarily in combinations of apparatus components and processing steps related to detection of leaks in a catheter in the presence of an electrical interferer. Accordingly, components have been represented where appropriate by conventional symbols in the drawings, showing only those specific details that are pertinent to understanding the embodiments so as not to obscure the disclosure with details that will be readily apparent to those of ordinary skill in the art having the benefit of the description herein. Like numbers refer to like elements throughout the description.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Figure 2:
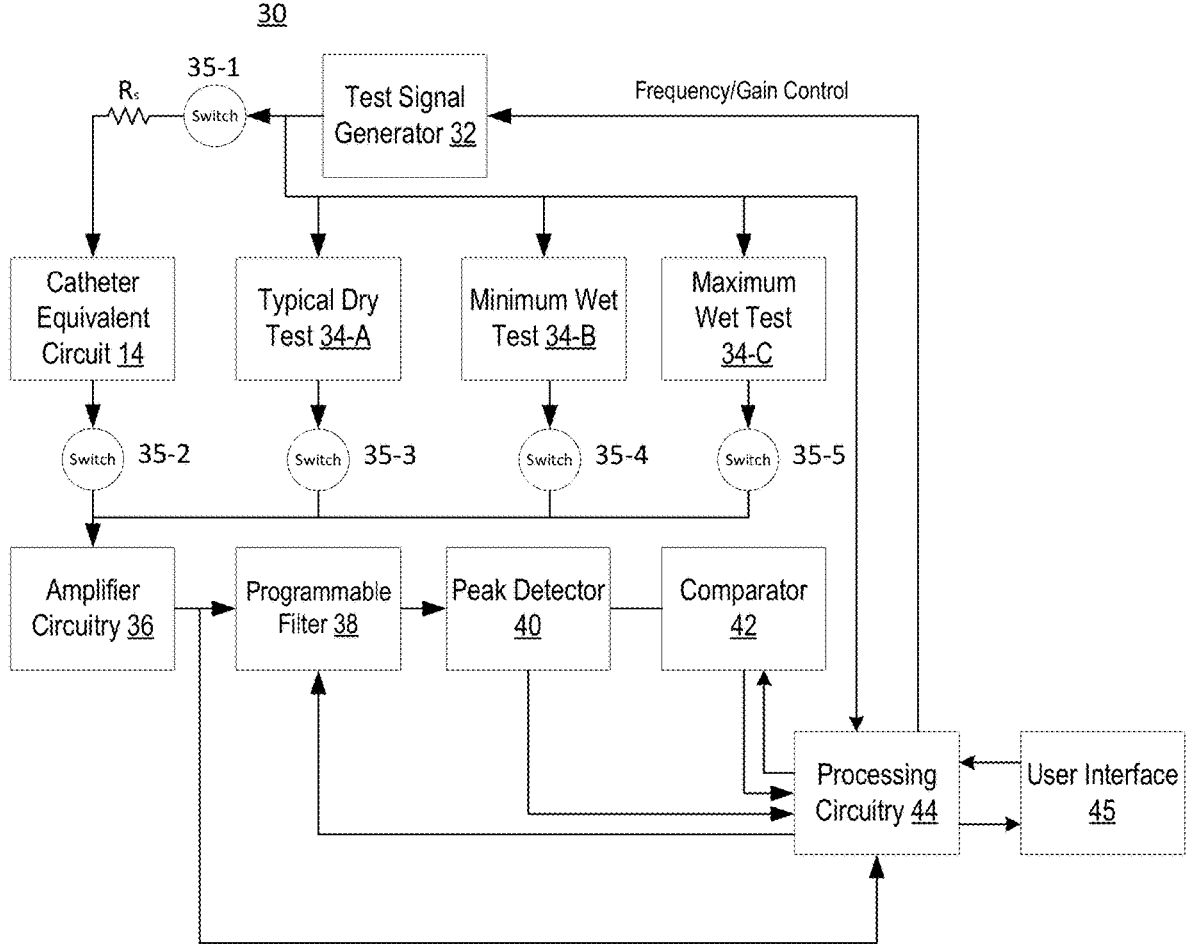
FIG. 2 is a block diagram of a catheter leak detection system constructed according to principles set forth herein.

Referring again to the drawing figures, FIG. 2 is a block diagram of one example embodiment of a leak signal discriminator 30 according to principles set forth herein. For clarity, some components of some embodiments of the leak signal discriminator 30 are not shown in FIG. 2. Also, in some embodiments, less than all components and/or connections shown in FIG. 2 are present. A test signal generator 32 generates and outputs a current that is a sum of sine waves, each sine wave being at a different frequency. In some embodiments, no one frequency of a sine wave is an integer multiple of a frequency of any of the other sine waves. The output of the test signal generator 32 is input to a switch 35-1 which is closed when performing leak detection. When the switch 35-1 is closed, current oscillating at the frequencies of the sine waves generated by the test signal generator 32 flows through the switch 33 and through a current limiting resistor $R_s$. A value of $R_s$ is about 6.2 kilo-Ohms (kΩ) in some embodiments. The current flowing through the resistor $R_s$ is applied to wires of the catheter. The catheter equivalent circuit 14 may be the equivalent circuit of a conventional catheter, or may be the equivalent circuit of a catheter to be developed in the future.

Within the catheter, the capacitance of the catheter equivalent circuit 14 will increase if fluid leaks into the catheter. This increase in capacitance will cause a change or modulation of the amplitude of the current flowing through the catheter equivalent circuit 14. Further, the modulation may be frequency dependent, so that the current flowing through the catheter equivalent circuit 14 is modulated differently at the different frequencies of the sine waves generated by the test signal generator 32. This difference in modulation at different frequencies provides at least one way to differentiate modulation arising from a leak and modulation arising from an electrical interference signal.

The output of the catheter equivalent circuit 14 passes through the switch 35-2, which is closed during a leak detection test. The output from the switch 35-2 is input to amplifier circuitry 36, which amplifies and filters the current received from the catheter equivalent circuit 14. Thus, when switches 35-1 and 35-2 are closed, the leak discriminator circuit 30 is configured to test to determine if there is a mechanical breach or leak of the catheter shaft in the presence of an electrical interferer. Conversely, when switches 35-1 and 35-2 are open, the leak discriminator circuit 30 may be configured to perform one or more diagnostic tests 34-A, 34-B and 34-C, for example. Diagnostic test 34-A is a typical dry test module that is connected to the amplifier circuitry 36 via a switch 35-3 and that provides internal loop back to emulate a typical dry catheter load (e.g., a no leak load of 6.2 kilo-Ohms and 220 pico-Farads). Diagnostic test 34-B is a minimum wet test module that is connected to the amplifier circuitry 36 via a switch 35-4 and that provides internal loop back to emulate a minimum wet threshold catheter load (e.g., a real leak load of 6.2 kilo-Ohms and 470 pico-Farads or above). Diagnostic test 34-C is a maximum wet test that is connected to the amplifier circuitry 36 via a switch 35-5 and that provides internal loop back to emulate a full wet catheter load (e.g., a wet catheter load of 6.2 kilo-Ohms).

The bandwidth of the filtering provided by the amplifier circuitry 36 is sufficient to pass all of the sine waves generated by the test signal generator 32. The amplified, filtered signal from the amplifier circuitry 36 is input to a programmable filter 38. As will be explained in further detail below, the programmable filter 38 selectively filters the amplified, filtered signal from the amplifier circuitry 36.

Note that the processing circuitry 44 is shown in FIG. 2 as receiving various inputs and providing various outputs. For example, the output of the test signal generator 32 may be divided or attenuated and input to the processing circuitry 44. The divided or attenuated output of the test signal generator 32 may be used by the processing circuitry 44 as a reference signal. The reference signal may be compared to the output of the amplifier circuitry 36, which output is fed to the processing circuitry 44. Comparing the reference signal to the amplifier circuitry output provides another way to distinguish between a valid leak signal and an interfering signal. Also, the output of the test signal generator may be calibrated by the processing circuitry to be at a certain amplitude or have a certain relative phase. The processing circuitry 44 may also provide gain and frequency control signals to the test signal generator 32. The processing circuitry 44 may also be configured to provide a clock signal and a filter selection signal to the programmable filter 38 to control the frequency parameters of the programmable filter 38 and to select a frequency band for each of one or more of the sine waves modulated by the catheter equivalent circuit 14. This provides another way to distinguish or discriminate between a signal caused by an actual leak or breach in the catheter and an interfering signal in a non leaking catheter.

Figure 3:
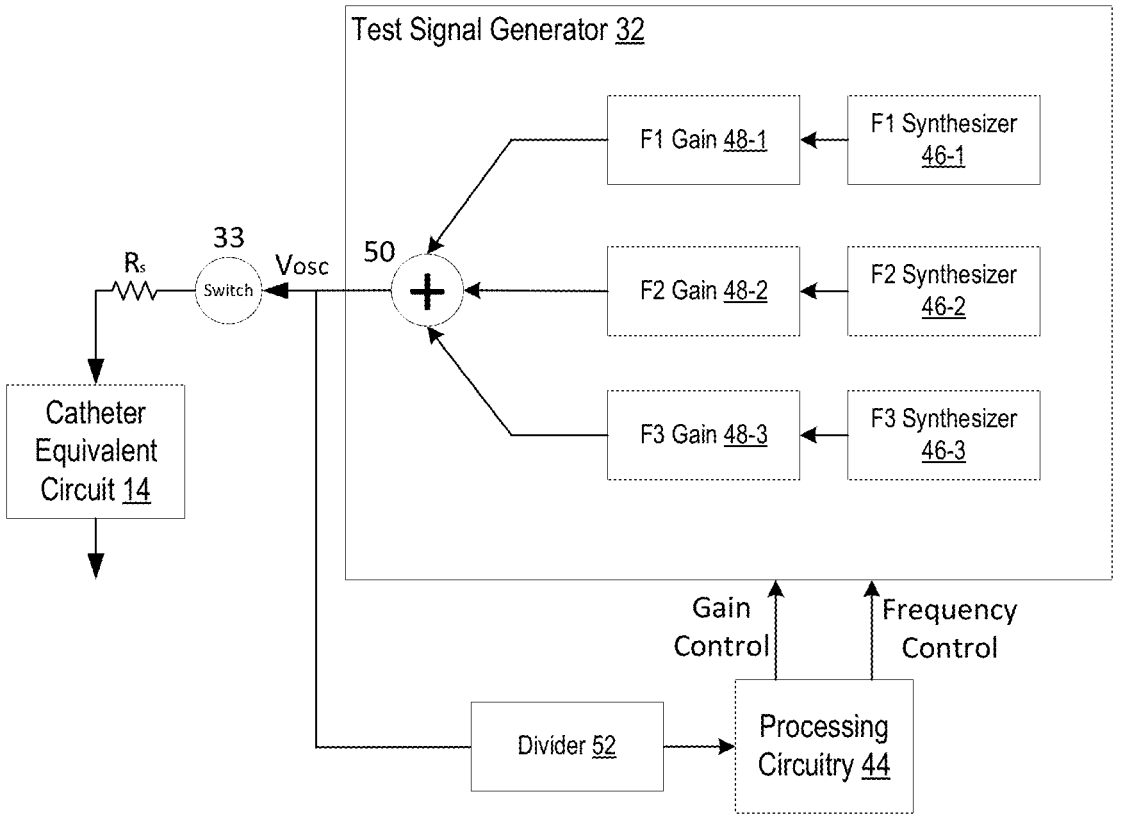
FIG. 3 is a block diagram of a multi-frequency test signal generator.

A block diagram of one example embodiment of the test signal generator 32 is shown in FIG. 3. The test signal generator 32 includes two or more frequency synthesizers 46 (also referred to herein as oscillators), each frequency synthesizer 46 being configured to generate a sine wave at a different frequency. An example of a set of frequencies that may be generated by the frequency synthesizers 46 is 15 kilo-Hertz (kHz), 25 kHz and 40 kHz. Another example of a set of frequencies is 25 kHz, 40 kHz and 60 kHz. The frequencies of the synthesizers may be selected by a user via the user interface 45. The frequencies may be selected according to an algorithm executed by the processing circuitry 44. Following each frequency synthesizer 46 is a gain module 48. Each gain module 48 is configured to controllably amplify a respective one of the sine waves generated by the frequency synthesizers 46. The gain may be selected by a user via the user interface 45. In some embodiments, the gain for each sine wave may be determined by the processing circuitry 44 according to an algorithm. For example, when the amplitude of a sine wave detected by the amplifier circuitry 36 exceeds some threshold, the amplitude for that sine wave may be reduced.

The sine waves from the different gain modules 48 are summed by an adder 50 to produce the voltage signal $V_{osc}$. The voltage signal $V_{ose}$ may be divided or attenuated by a divider 52, to be used as a reference signal by the processing circuitry 44 to be compared to the amplified signal output from the amplifier circuitry 36. The voltage signal $V_{ose}$ is also input to the catheter equivalent circuit 14 via the resistor $R_s$. Note that although FIG. 3 shows generation of three different sine waves, any number of sine waves greater than 1 may be implemented according to principles disclosed herein.

Figure 4:
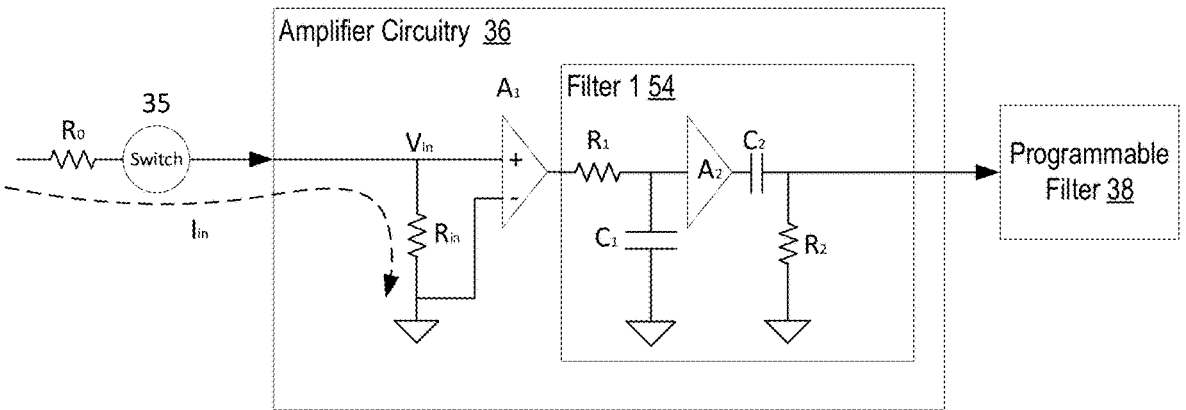
FIG. 4 is a circuit diagram of amplifier circuitry.

FIG. 4 is a circuit diagram of one example embodiment of the amplifier circuitry 36. The amplifier receives the current $I_{in}$ from the catheter equivalent circuit 14 via a resistor $R_0$ and a switch 35. The current $I_{in}$ flows through a resistor $R_{in}$, thereby developing a voltage $V_{in}$ at the input of a first amplifier $A_1$. Amplifier $A_1$ may be a differential input instrumentation amplifier (INA) that rejects common mode signals. In some embodiments, $R_{in}$ is 200 ohms. In some embodiments, the amplifier $A_1$ has a gain of about 25. The amplifier $A_1$ amplifies the voltage $V_{in}$ and outputs the amplified voltage to a first filter 54. The first filter 54 includes a low pass filter formed by resistor $R_1$ and capacitor $C_1$ a second amplifier $A_2$, and a high pass filter formed by capacitor $C_2$ and resistor $R_2$. The filter topology shown in FIG. 4 is but one example. Other filter topologies may be implemented to filter out high frequency signals, and block potential DC offsets and very low frequency components of potential interferers, such as at 60 Hz. The first filter 54 has a pass band positioned to pass all of the sine waves from the test signal generator 32. The output of the amplifier circuitry 36 is input to the programmable filter 38.

Figure 5:
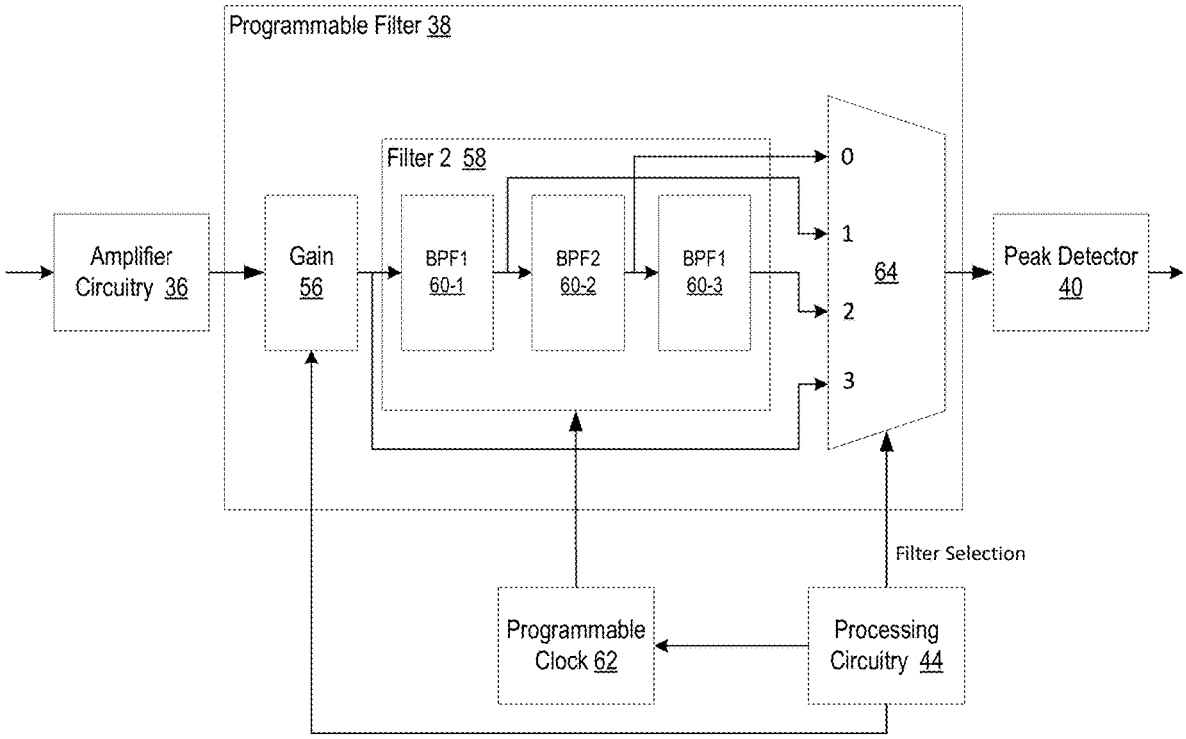
FIG. 5 is a block diagram of a programmable band pass filter.

FIG. 5 is a block diagram of the programmable filter 38. A gain module 56 is controllable by the processing circuitry 44 to amplify or attenuate the signal from the amplifier circuitry 36. Attenuation by the gain module 56 may be employed to avoid clipping. The output of the gain module is input to a second filter 58. The second filter 58 includes a series of bandpass filter stages 60-1, 60-2 and 60-3. Although three band pass filter stages are shown in FIG. 5, more generally there may be one bandpass filter stage 60 for each different sine wave generated by the test signal generator 32. Also, the three band pass filter stages may be selectively bypassed by the processing circuitry 44. The filter characteristics of the individual bandpass filter stages 60 may be controllable by a programmable clock 62 having a clock frequency that is settable by the processing circuitry 44. The bandpass filter stages 60 are configured so that one or more bandpass filter stages 60 are selectable to pass only one of the frequencies of the sine waves generated by the test signal generator 32 and reject the other frequencies. In some embodiments, each of the bandpass filter stages 60 are of identical order.

A multiplexer 64 having a number of inputs equal to one plus the number of bandpass filter stages 60, is controllable by the processing circuitry 44 to select an output of one of the bandpass filter stages 60 or to select no filtering at all. Thus, for the example of FIG. 5, when port 3 of the multiplexer 64 is selected, all bandpass filter stages 60 are bypassed. When port 2 of the multiplexer 64 is selected, the signal input to the second filter 58 passes through all bandpass filter stages 60. For example, if each bandpass filter stage 60 is a second order filter, then selection of port 2 results in a sixth order filter. When port 1 of the multiplexer 64 is selected, a signal passing through only the first one of the bandpass filter stages 60 is selected. When port 0 of the multiplexer 64 is selected, the selected signal is the one that passes through the first two bandpass filter stages 60-1 and 60-2 of the second filter 58 to produce fourth order filtering. The output of the multiplexer 64 is input to the peak detector 40.

Figure 6:
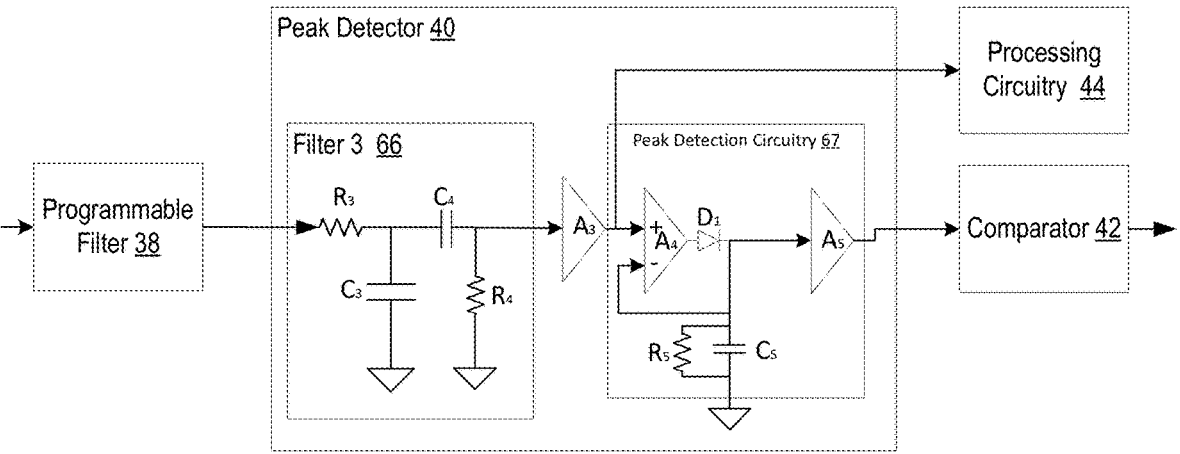
FIG. 6 is a circuit diagram of a peak detector.

FIG. 6 is a circuit diagram of one example of the peak detector 40. The peak detector 40 may include a third filter 66 that includes a low pass filter formed by resistor $R_3$ and capacitor $C_3$, and a high pass filter formed by capacitor $C_4$ and resistor $R_4$. Other filter topologies may be employed. In the circuit diagram of FIG. 6, the cutoff frequencies of the low pass filter and the high pass filter of the third filter 66 may be arranged to form a pass band to pass any one or more of the sine waves generated by the test signal generator 32. The output of the third filter 66 is amplified by a third amplifier $A_3$. The output of the third amplifier $A_3$ may be sent to the processing circuitry 44 for application of digital signal processing routines to digitally filter the output of the third amplifier to further differentiate between a signal due to a leak and a signal due to an electrical interferer. The output of the third amplifier $A_3$ may also be compared by the processing circuitry 44 to the output of the amplifier circuitry 36 when the band pass filters 60 are by passed in order to assess the operation of the filter 58. The output of the amplifier $A_3$ is further amplified by a fourth amplifier $A_4$. The fourth amplifier $A_4$ is part of peak detection circuitry 67 that also includes resistor $R_5$ in parallel with capacitor $C_5$. A diode D1 is used in a feedback loop together with the amplifier A4 to behave as an ideal diode that captures the peak positive level of the input to the amplifier A4. This peak positive level is stored by capacitor C5 for a preservation time determined by the resistor R5. The choice of the ideal diode configuration enables C5 to discharge to 0 volts, rather than to 0.7 volts, for example, for a typical diode component. This means that the final discharge value of C5 will not be a significant portion of the range of peak values to be detected by the peak detection circuitry 67. Further, the ideal diode that includes D1 and $A_4$ is more stable with respect to temperature than a typical diode component. A fifth amplifier $A_5$ further amplifies the output of the peak detection circuitry 67 and sends the amplified output of the peak detection circuitry to the comparator 42. The amplifier A5 may be powered by a +5 volt to −12 volt power supply.

Figure 7:
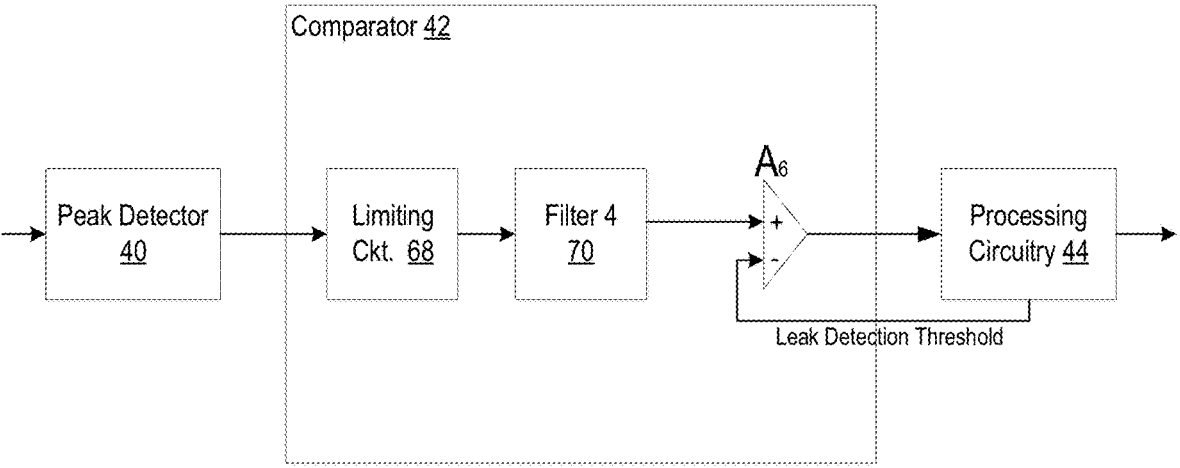
FIG. 7 is a block diagram of a comparator.

FIG. 7 is a block diagram of the comparator 42. A limiting circuit 68 limits positive and negative swings of the output of the peak detector 40. The output of the limiting circuit 68 is filtered by a fourth filter 70 and input to the sixth amplifier $A_6$. The input to the sixth amplifier may be clipped by the clipping circuit to between 3.6 and −0.3 volts and protects amplifier $A_6$ from unexpected overvoltage. The sixth amplifier $A_6$ is a hysteresis amplifier. When the input from the fourth filter 70 rises above a leak detection threshold set by the processing circuitry 44, an output of the amplifier $A_6$ changes state to a leak detection alarm indication state. When the output of the fourth filter falls below the leak detection threshold, the output of the amplifier $A_6$ remains in the leak detection alarm indication state until the output of the fourth filter falls below a second threshold lower than the leak detection threshold, at which time the amplifier output returns to its former non-alarm state. The alarm indication state of the amplifier output is signaled to the processing circuitry 44, which indicates to the user, via the user interface 45, whether a leak has been detected.

Thus, the output of the multiplexer 64 may be input to the peak detector 40 and also digitized by an analog to digital converter (ADC) and input to the processing circuitry 44. The peak detector 40 may detect a positive peak of the output of the multiplexer 64 and output a DC value proportional to the amplitude of the peak, in some embodiments. The DC value may be input to the comparator 42 resulting in a binary output monitored by the processing circuitry 44. The DC value may also be monitored by a low speed ADC input to the processing circuitry 44. The output of the multiplexer 64 may be input to an ADC input of the processing circuitry 4 which samples the input waveform at a relatively high speed compared to the low speed ADC. The digitized input waveform may be processed by digital signal processing algorithms to differentiate between a leak and an electrical interferer.

Figure 8:
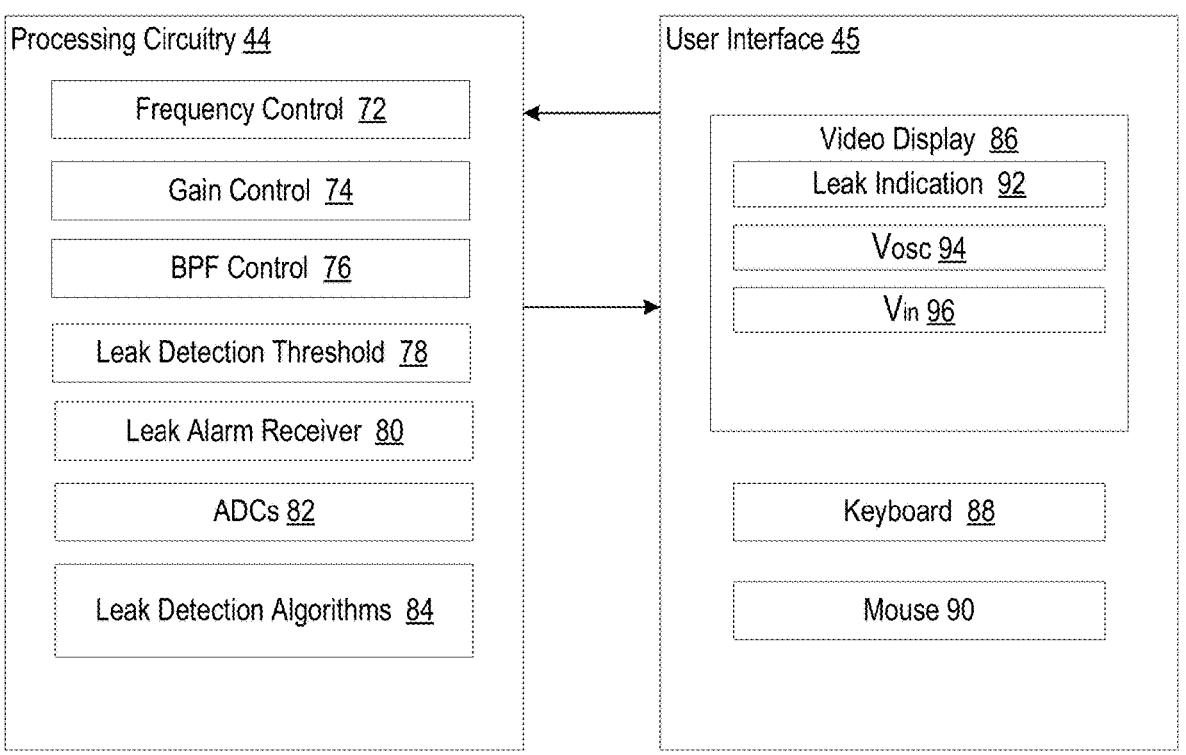
FIG. 8 is a block diagram of processing circuitry in communication with a user interface.
Figure 9:
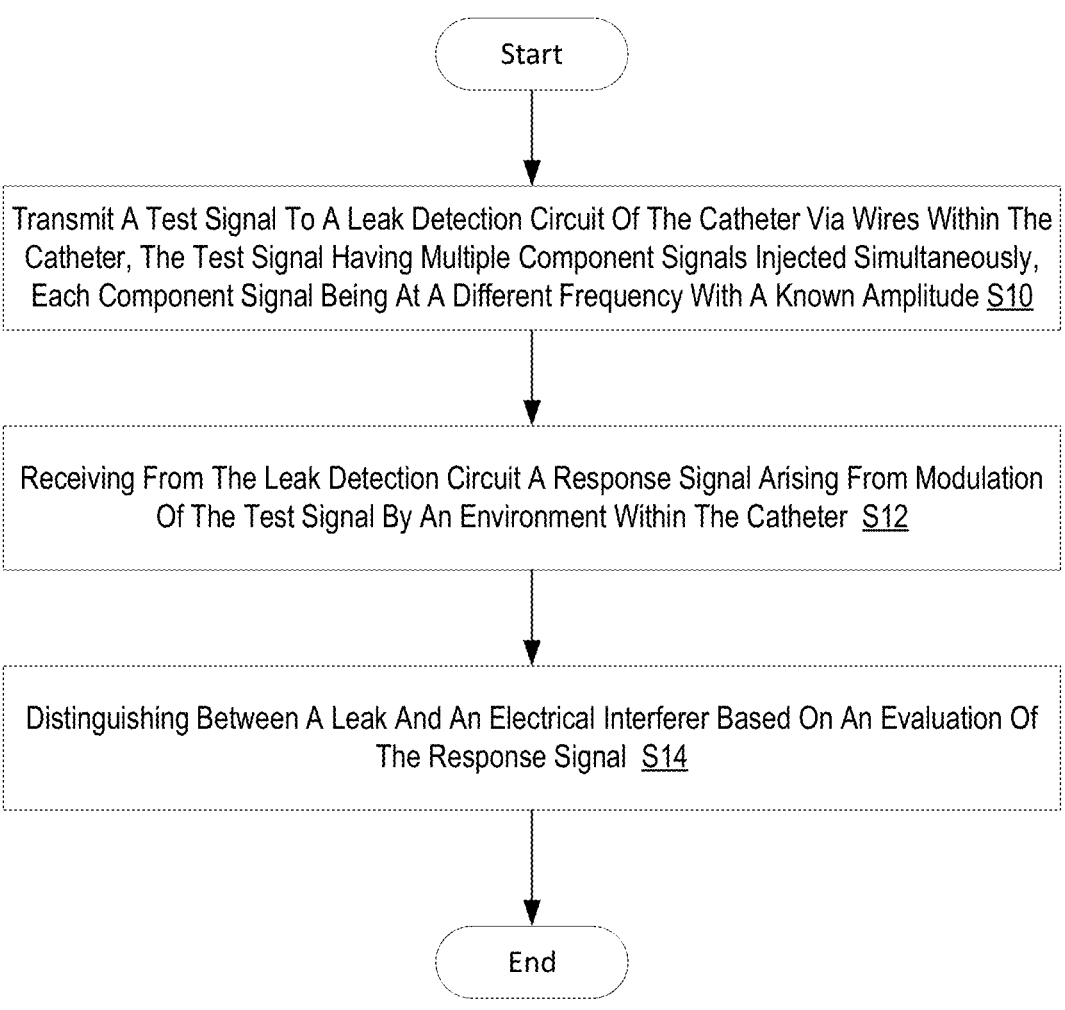
FIG. 9 is a flowchart of an example process for distinguishing between a leak and an electrical interferer.

FIG. 8 is a block diagram of the processing circuitry 44 in communication with the user interface 45. The processing circuitry may be implemented as a processor operating under the directions of computer code stored in an electronic memory. The processing circuitry 44 may be implemented in whole or in part by application specific integrated circuitry (ASIC) and/or field programmable gate arrays (FPGAs). The processing circuitry 44 may have functionality to perform frequency control 72 over the frequency of the sine waves generated by the test signal generator 32 and may also have functionality to perform gain control 74 over the gain modules 48 of the test signal generator 32. The processing circuitry 44 further may have bandpass filter control functionality 76 to control the passbands of the bandpass filter stages 60 of the programmable filter 38. The bandpass filter control functionality 76 may further include selecting which bandpass filter stages 60 are applied to the signal received from the amplifier circuitry 36. The processing circuitry 44 may further set the leak detection threshold 78 used by the comparator 42 to determine whether to signal a leak detection alarm state. A leak alarm receiver 80 receives a leak detection alarm signal from the comparator 42 and determines whether to indicate to a user a leak condition via the user interface 45. The processing circuitry 44 also includes a plurality of analog to digital converters (ADCs) 82 to convert analog signals to a digital form prior to using these signals as inputs to leak detection algorithms 84. The analog signals may include a signal from the output of the amplifier A3 in FIG. 6, a signal that bypasses the bandpass filters 60 in FIG. 5, and/or the signal that is output by the amplifier circuitry 36. One or more of these analog signals, once digitized, allow the processing circuitry 44 to perform leak detection algorithms. Leak detection algorithms 84 distinguish between a leak signal and an interference signal. In some embodiments, the execution of the leak detection algorithms 84 may be conditioned upon whether an output of the comparator 42 indicates a leak. The leak detection algorithms 84 may be configured to differentiate between a leak and an electrical interferer even when the electrical interferer interferes at a frequency within a pass band of the band pass filters 60.

The user interface 45 may include a video display device 86 such as a flat screen monitor to enable visual display of information to the user. The user interface 45 also includes a keyboard 88 and a mouse 90 to enable user input of such parameters as the frequencies of the sine waves generated by the test signal generator 32, the bandwidth of each bandpass filter stage 60 of the programmable filter 38, a leak detection threshold 78, etc. The video display device 86 may include a display of a leak detection indication 92, a display of one or more of the sine waves generated by the test signal generator 32, a display of $V_{ose}$ 94, a display of $V_{in}$ 96, etc. The video display 86 may display an alert that there are interferers present and/or an indication to check for the presence of interferers.

The leak signal discriminator 30 may employ one or more of several different leak detection algorithms 84. The leak detection algorithm that is selected may be implemented in hardware and/or software. Some or all of the steps of a leak detection algorithm may be performed in whole or in part in the hardware external to the processing circuitry 44 discussed above, based at least in part on signals from the processing circuitry 44. Consequently, the leak signal discriminator 30 may implement one or leak detection mechanism which may include, at least in part, the execution of computer code. In some embodiments, if one leak detection mechanism indicates a leak, another leak detection mechanism may be selected to confirm the leak.

In a first leak detection mechanism, the output $V_{ose}$ of the test signal generator 32 is compared to the input $V_{in}$ to the amplifier circuitry 36 or to the output of the amplifier circuitry 36. The relative phase between $V_{ose}$ and $V_{in}$ or the amplifier circuitry output may be used as an indication of whether there is a leak in the catheter or whether a spurious interfering signal has caused a false indication of a leak. The first leak detection mechanism may be useful when the interfering signal has a frequency very close to a frequency of a sine wave included in $V_{osc}$.

In a second leak detection mechanism, the signal $V_{in}$ that is input to the amplifier $A_1$ is sampled at a rate that is sampled at a sampling rate that is a multiple of the frequency of one of the sine waves generated by the test signal generator 32, but not a multiple of the frequencies of the other sine waves generated by the test signal generator 32. This second leak detection mechanism discriminates against interfering signals that are not close to the frequency of the sine wave of which the sampling rate is a multiple. In some embodiments, each of a plurality of the sine waves generated by the test signal generator 32 will be sampled at a rate that is a multiple of the respective frequency of the sine wave. When a leak signal is indicated at a first frequency, a second sine wave at a second frequency is sampled to determine if a leak is indicated at the second frequency. If so, it is likely to be a true leak. Otherwise, a true leak is not declared by the second leak detection mechanism.

In a third leak detection mechanism, the peak detection circuitry 67 produces a signal that is a simple analog DC level that is amplified by the amplifier $A_5$. The amplified analog DC signal is compared by the comparator 42 to a programmable threshold to determine whether to declare the presence of a true leak in the catheter.

In a fourth leak detection mechanism, when a leak is detected by one of the leak detection mechanisms discussed above, the output $V_{ose}$ of the test signal generator 32 is turned off to verify that the signal in which the leak is detected originates from the test signal generator 32, and not from an electrical interferer. For example, when the test signal generator 32 is turned off and a leak is still detected, the processing circuitry 44 may conclude that a leak is not present.

In a fifth leak detection mechanism, the third leak detection mechanism is used to monitor for interference on a frequency of a first sine wave generated by the test signal generator 32. In this fifth leak detection mechanism, the leak detection threshold for a second frequency of a second sine wave generated by the test signal generator 32 is set based at least in part on the monitoring.

In a sixth leak detection mechanism, if the second, third and fourth leak detection mechanisms indicate a leak, the first leak detection mechanism can be used to confirm the leak.

In one aspect, the present disclosure provides a method of distinguishing between a leak signal arising from a leak in a catheter and an interfering signal arising from an electrical interferer. The method includes transmitting a test signal generated by the test signal generator 32 to a catheter equivalent circuit 14 via wires within the catheter, the test signal having multiple component signals injected simultaneously, each component signal being at a different frequency with a known amplitude. The method also includes receiving from the catheter equivalent circuit 14 a response signal arising from modulation of the test signal by an environment within the catheter. The method further includes distinguishing between a leak and an electrical interferer based at least in part on an evaluation of the response signal.

According to this aspect, in some embodiments, distinguishing between a leak and an electrical interferer includes filtering, via the programmable filter 38, the response signal at a first frequency of the different frequencies to produce a first filtered response signal. In some embodiments, distinguishing between a leak and an electrical interferer further includes: comparing, via the comparator 42, the first filtered response signal to a first threshold. When the filtered response signal exceeds the first threshold, then the method includes filtering, via the programmable filter 38, the response signal at a second frequency of the different frequencies to produce a second filtered response signal; comparing, via the comparator 42, the second filtered response signal to a second threshold. When the second filtered response signal exceeds the second threshold, then a leak is indicated. In some embodiments, at least one of the first threshold and the second threshold is set, via the processing circuitry 44, according to a measure of noise power in the response signal. In some embodiments, the measured noise power for setting the first threshold is measured at a frequency that is different than the first frequency. In some embodiments, distinguishing between a leak and an electrical interferer includes passing the response signal through a programmable filter 38 configured to pass the response signal at one of the different frequencies and filter out the other frequencies of the different frequencies. In some embodiments, the filter 38 is programmable to select a center frequency of the filter. In some embodiments, the filter 38 is programmable to select an order of the filter. In some embodiments, distinguishing between a leak and an electrical interferer further includes turning off the test signal to determine whether the evaluation of the response signal indicates a presence of an electrical interferer when the test signal is turned off. In some embodiments, no component signal frequency is an integer multiple of any other of the component signal frequencies.

According to another aspect, a leak signal discriminator 30 having a catheter equivalent circuit 14, the leak signal discriminator 30 being configured to distinguish between a leak signal arising from a leak in a catheter and an interfering signal arising from an electrical interferer. The leak signal discriminator 30 includes circuitry configured to receive from the catheter equivalent circuit 14 a response signal responsive to a test signal the test signal having component signals, each component signal being at a different frequency; and distinguish between a leak and an electrical interferer based at least in part on an evaluation of the response signal.

According to this aspect, in some embodiments, distinguishing between a leak and an electrical interferer includes filtering, via the programmable filter 38, the response signal at a first frequency of the different frequencies to produce a first filtered response signal. In some embodiments, distinguishing between a leak and an electrical interferer further includes: comparing, via the comparator 42, the first filtered response signal to a first threshold. When the first filtered response signal exceeds the first threshold, then, the response signal is filtered, via the programmable filter 38, at a second frequency of the different frequencies to produce a second filtered response signal. The leak signal discriminator 30 is configured to compare, via the comparator 42, the second filtered response signal to a second threshold, and when the second filtered response signal exceeds the second threshold, then indicating a leak. In some embodiments, at least one of the first threshold and the second threshold is set, via the processing circuitry 44, according to a measure of noise power in the response signal. In some embodiments, the measured noise power for setting the first threshold is measured at a frequency that is different than the first frequency. In some embodiments, the leak signal discriminator 30 further includes a filter 38 configured to pass the response signal at one of the different frequencies and filter out the other frequencies of the different frequencies. In some embodiments, the filter 38 is programmable to select a center frequency of the filter. In some embodiments, the filter 38 is programmable to select an order of the filter. In some embodiments, the leak signal discriminator 30 further includes a peak detector 40 configured to measure an amplitude peak of the response signal. In some embodiments, distinguishing between a leak and an electrical interferer further includes turning off the test signal to determine whether the evaluation of the response signal indicates a presence of an electrical interferer when the test signal is turned off. This may be done autonomously by the processing circuitry 44.

According to yet another aspect, a cryoablation system 30 is configured to distinguish between a leak signal arising from a leak in a catheter of the cryoablation system 30 and an interference signal arising from an electrical interferer. The system includes a test signal generation circuit 32 having a plurality of oscillators or frequency synthesizers 46, each oscillator 46 being configured to oscillate at a different frequency, no one of the different frequencies being an integer multiple of any other of the different frequencies. The cryoablation system 30 also includes a catheter equivalent circuit 14 located within the catheter and configured to: receive the test signal and, responsive to the test signal, and send a response signal to a leak signal discriminator circuit which includes the amplifier circuitry 36, the programmable filter 38, the peak detector 40, the comparator 42 and the processing circuitry 44. The system also includes the leak signal discriminator circuit, the leak discriminator circuit configured to distinguish between a leak and an electrical interferer based at least in part on an evaluation of the response signal sent from the catheter equivalent circuit 14, the evaluating being performed at each of multiple ones of the different frequencies.

According to this aspect, in some embodiments, the cryoablation system 30 further includes a sampling circuit within the processing circuitry 44, configured to simultaneously sample the test signal and the response signal and compare the sampled test signal to the sampled response signal. In some embodiments, the response signal is sampled at a rate that is an integer multiple of one of the different frequencies. In some embodiments, the response signal is sampled at a rate that is an integer multiple of one of the different frequencies but not an integer multiple of the other frequencies of the different frequencies.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope of the following claims.

What is claimed is:

1. A method of distinguishing between a leak signal arising from a leak in a catheter and an interfering signal arising from an electrical interferer, the method comprising:
   transmitting a test signal to a leak detection circuit of the catheter within the catheter, the test signal having multiple component signals injected simultaneously, each component signal being at a different frequency with a known amplitude;
   receiving from the leak detection circuit a response signal arising from modulation of the test signal by an environment within the catheter; and
   distinguishing between a leak and an electrical interferer based on an evaluation of the response signal by filtering the response signal at a first frequency of the different component signal frequencies to generate a first filtered response signal.

2. The method of claim 1, wherein distinguishing between the leak and the electrical interferer includes:
   comparing the first filtered response signal to a first threshold; and
   when the first filtered response signal exceeds the first threshold:
      filtering the response signal at a second frequency of the different component signal frequencies to generate a second filtered response signal;
      comparing the second filtered response signal to a second threshold; and
      when the second filtered response signal exceeds the second threshold, indicating a leak.

3. The method of claim 2, wherein the first threshold and the second threshold are set according to a measured noise power in the response signal.

4. The method of claim 3, wherein the measured noise power for setting the first threshold is measured at a frequency that is different than the first frequency.

5. The method of claim 1, wherein distinguishing between the leak and the electrical interferer includes turning off the test signal to determine whether the evaluation of the response signal indicates a presence of an electrical interferer when the test signal is turned off.

6. The method of claim 1, wherein no one component signal frequency is an integer multiple of any other of the different component signal frequencies.

7. The method of claim 1, wherein the method includes measuring, via a peak detector, an amplitude peak of the response signal.

8. The method of claim 1, wherein distinguishing between the leak and the electrical interferer includes selecting an order of a filter to filter the response signal at the first frequency.

9. A method of distinguishing between a leak signal arising from a leak in a catheter and an interfering signal arising from an electrical interferer, the method comprising:
   transmitting a test signal to a leak detection circuit of the catheter within the catheter, the test signal having multiple component signals injected simultaneously, each component signal being at a different frequency with a known amplitude;
   receiving from the leak detection circuit a response signal arising from modulation of the test signal by an environment within the catheter; and
   distinguishing between a leak and an electrical interferer based on an evaluation of the response signal by passing the response signal through a filter configured to pass the response signal at one of the different component signal frequencies and filter out other frequencies of the different component signal frequencies.

10. The method of claim 9, wherein distinguishing between the leak and the electrical interferer includes selecting a center frequency of the filter.

11. The method of claim 9, wherein distinguishing between the leak and the electrical interferer includes selecting an order of the filter.

12. The method of claim 9, wherein distinguishing between a leak and an electrical interferer includes turning off the test signal to determine whether the evaluation of the response signal indicates a presence of an electrical interferer when the test signal is turned off.

13. The method of claim 9, wherein no one component signal frequency is an integer multiple of any other of the different component signal frequencies.

14. The method of claim 9, wherein the method includes measuring, via a peak detector, an amplitude peak of the response signal.

15. The method of claim 9, wherein the method includes:
   simultaneously sampling the test signal and the response signal; and
   comparing the sampled test signal to the sampled response signal.

16. The method of claim 15, wherein the response signal is sampled at a rate that is an integer multiple of one of the different component signal frequencies but not an integer multiple of other frequencies of the different component signal frequencies.

* * * * *